United States Patent [19]
Lavery

[11] Patent Number: 5,948,431
[45] Date of Patent: Sep. 7, 1999

[54] MEDICATED ANIMAL FOODSTUFFS

[75] Inventor: Martin Lavery, Preston, United Kingdom

[73] Assignee: Vericore Limited, Lancashire, United Kingdom

[21] Appl. No.: 08/860,979

[22] PCT Filed: Jan. 16, 1996

[86] PCT No.: PCT/GB96/00073

§ 371 Date: Jul. 15, 1997

§ 102(e) Date: Jul. 15, 1997

[87] PCT Pub. No.: WO96/22028

PCT Pub. Date: Jul. 25, 1996

[30] Foreign Application Priority Data

Jan. 17, 1995 [GB] United Kingdom .................... 9500863

[51] Int. Cl.$^6$ ....................................................... A23K 1/18
[52] U.S. Cl. ........................... 424/438; 424/442; 426/54; 426/807
[58] Field of Search ..................... 424/438, 442; 426/54, 807

[56] References Cited

U.S. PATENT DOCUMENTS

| | | | |
|---|---|---|---|
| 3,639,637 | 2/1972 | Campbell | 424/346 |
| 4,089,979 | 5/1978 | Jackson | 426/69 |
| 5,000,943 | 3/1991 | Scaglione | 424/57 |
| 5,011,679 | 4/1991 | Spanier | 424/57 |
| 5,650,184 | 7/1997 | Humphry | 426/89 |
| 5,698,246 | 12/1997 | Villamar | 426/54 |

FOREIGN PATENT DOCUMENTS

| | | |
|---|---|---|
| 0231817 | 8/1987 | European Pat. Off. . |
| 0241441 | 10/1987 | European Pat. Off. . |
| 0658313 | 6/1995 | European Pat. Off. . |
| 4325658 | 2/1995 | Germany . |
| 59-063147 | 7/1984 | Japan . |
| 60-012939 | 1/1985 | Japan . |
| 680896 | 12/1992 | Switzerland . |
| 2203336 | 10/1988 | United Kingdom . |

*Primary Examiner*—D. Gabrielle Brouillette
*Attorney, Agent, or Firm*—Dann, Dorfman, Herrell and Skillman

[57] ABSTRACT

A method of adding a medicament (or other added ingredient) to animal feed pellets is described, in which the medicament is contained in a cohesive gel which is mixed with the feed pellets. The gel coats the pellets substantially homogeneously, and leaves little contamination of the mixing vessel.

12 Claims, No Drawings

MEDICATED ANIMAL FOODSTUFFS

This application is a 371 of PCT/GB96/00073, filed Jan. 16, 1996.

This invention relates to methods for incorporating feed ingredients (particularly, but not exclusively, medicaments) with animal foodstuffs, and to substances useful in such methods.

Treatment of intensively farmed animals with medication is often carried out by "mass medication", that is to say that animals are not treated individually, but as a group. The most efficient way of doing this is by adding the treatment to the animals' feed or drink. Water medication is very labour intensive and may require veterinary supervision, and longer term treatments are much more easily carried out by supplying the group of animals with medicated feed.

Manufactured foodstuffs for animals such as cattle, pigs, and fowl are usually provided in the form of pellets or similar particulate material. Pellets are typically manufactured by combining a cereal base with ingredients such as oil and protein, steam conditioning the mixture (for example at 70° C. for 5 minutes), extruding through a circular die (typically between 2 mm and 15 mm in diameter), cutting into appropriately sized lengths (eg. 5–20 mm), and drying. The finished pellets are generally cylindrically shaped, having a relatively smooth surface, and a density typically of about 1.2 g.cm$^{-3}$.

Conventionally, additives such as drugs are incorporated into the feed mixture before the extrusion step. However, because many different drugs are required to be added to feed pellets from time to time, and because the demand for any particular medicated product is generally relatively low compared to the demand for non-medicated feed, it is not usually viable to provide dedicated plant for manufacturing specific products. Instead, batches of medicated feed are manufactured according to need using machinery otherwise used to produce non-medicated feed. A major problem with this manufacturing regime is that the plant needs to be completely cleaned down after the production of each batch of medicated feed, in order to reduce the risk of contaminating subsequent feed batches. This obviously reduces efficiency and increases operating costs.

The addition of active agents to individual batches of feed could be carried out more cost-effectively "off-line", that is to say with non-medicated feed pellets being manufactured continuously, and those batches which require medication being transferred to a separate plant for addition of medicament.

This would require the application of the medicament to the surfaces of the finished pellets, and attempts have been made to accomplish this in the past. However, no reliable technology currently exists to enable medications to be routinely and reproducibly added to the external surface of feed pellets and to remain there during transport and use.

It has now surprisingly been found that reliable homogeneity of active ingredient in the finished feed can be achieved by coating the pellets with a cohesive gel containing the active ingredient. It has furthermore been surprisingly found that gel coating according to the invention tends to leave the feed mixing vessel in which the coating is carried cut substantially free from active agent contamination. Because the coating method is not dependent upon the nature of the active ingredient, the invention will also be of use n adding other substances (such as nutritional supplements), and added ingredients in general.

The present invention therefore provides, in one aspect, a method of incorporating an added ingredient with an animal foodstuff, comprising the step of coating feed pellets (or similar particulate foodstuff material) with a cohesive gel containing said added ingredient.

In some instances, the pellets may be fed to animals directly after coating, but more commonly the gel is dried or absorbed into the pellet, thus entrapping the medication in the pellet and giving protection against attrition and the formation of active agent dust.

In this specification, the term "gel" is to be understood as referring to any viscous cohesive suspension, and the term "gelling agent" to any thickening agent capable of producing such a suspension. The gel is preferably a highly viscous solution or suspension (for example an aqueous suspension), having low flow and good adhesive properties. Thixotropic gels may be used. For the gel to behave as mentioned above, the viscosity should be controlled within the range 5,000 to 20,000 cP (Brookfield RV, spindle 6, 25 rpm, 20° C.), more preferably in the range 5,000 to 15,000 cP, and ideally in the range 7,500 to 12,500 cP. This viscosity range allows added ingredients having particles of a wide variety of sizes and densities to be homogeneously suspended, and also gives the gel the necessary cohesive properties for good feed pellet distribution and low mixer contamination.

Examples of suitable gelling agents which may be used for this purpose are modified cellulose polymers, synthetic polymers, natural polysaccharides, clays, proteins and colloidal silica, but other gelling agents may also be used. The gel can be supplied to users ready mixed with the added ingredient(s), or as a raw gel, for such ingredient(s) to be added. Alternatively, the gelling agent may be provided in powder form and made up to the finished gel when required, with the added ingredient(s) being either mixed in at the outset, or being added after the gel is made up. If the gelling agent is supplied in powder form, the mixing can be accomplished by adding water, oil, or another appropriate liquid, and mixing vigorously (for example in a high speed planetary mixer) to shear the mixture and allow complete hydration of the gelling agent. The amount of liquid will depend on the gelling agent used, and on the ratio of gelling agent to other ingredients in the powder; tonically the final gel will contain 1 to 50% w/w (preferably 1 to 10% w/w) of the gelling agent.

Examples of suitable modified cellulose polymers which may be used as the gelling agent are: sodium carboxymethylcellulose, methylcellulose, hydroxypropylmethylcellulose, hydroxymethylcellulose, hydroxypropylcellulose, ethylcellulose, hydroxyethylcellulose, and microcrystalline cellulose.

Examples of suitable synthetic polymers are: polyacrilic acid polymers (Carbomers), polyvinylpyrrolidones (PVPs), crospovidones, polyvinyl alcohols, and colloidal anhydrous silicas.

Examples of natural polysaccharides which may be used include: xanthan gum, acacia gum, agar, carrageenan and tragacanth.

Examples of suitable clays are bentonite and aluminium magnesium silicates, and an example of a suitable protein is gelatin.

The invention may be used to incorporate many different types of added ingredient or combinations of added ingredients. Examples of medicaments which may be used are: antimicrobials (such as tetracyclines, penicillins, sulphonamides, cephalosporins, cephamycins, aminoglycosides, aminocyclitols, trimethoprim, dimetridazole, erythromycin, framycetin, furazolidone, lincosamides, tiamulin, macrolides, and streptomycin); antiprotozoals (such as clopidol, monensin, salinomycin, narasin, halofuginone, lasalocid, amprolium, maduramicin, and robenidine); and antiparasitics (such as benzimidazoles, imidazothiazoles, avermectines, milbermycins, salicylicanilides and piperazine).

Examples. or other added ingredients are growth promoters (such as tylosin, virginiamycin, zinc bacitracin, avoparcin bambermycin., avilamycin); vaccines (for example to prevent *E. coli* infections); immunostimulants; vitamins (such as vitamin A, B group vitamins, vitamins C, D, E and K3); minerals (for example salts containing micronutrients, such as iron, zinc, copper, selenium, iodine, manganese, calcium and phosphorus); and enzymes. The concentration of total added ingredients in the gel will typically range from 0.5 to 10% w/w of the final gel.

Many products may also require a preservative (typically in a concentration of 0.05–59% w/w of the final gel), to prevent the growth of organisms in use. Examples of suitable preservatives are: parabens, benzoic acid and salts, propionic acid and salts, sorbic acid and salts, bronopol and formaldehyde.

The final formulations of the products may also include other adjuvants such as dispersing or wetting agents (such as surfactants e.g. Tweens, Brijs, sodium lauryl sulphate), buffering agents (such as citric acid and citrates, phosphoric acid and phosphates) and diluents (such as lactose, calcium carbonate, silica and starch).

The feed pellets and gel are preferably mixed relatively gently, to prevent the feed from disintegrating. Any low shear mixer with a blade which has a fine tolerance with the side of the mixing vessel is adequate, such as a planetary mixer or ribbon blender. The gel is gently added to (e.g. folded into) the feed pellets and slowly and uniformly coats them. The amount of gel added per tonne of feed appears to be critical and should be in the range 2–40 kg/tonne. Less than 2 kg/tonne gives poor product homogeneity, and over 40 kg/tonne gives rise to damp (i.e. overly wetted) feed and possible mould growth in the finished feed pellets; more typically the amount used is in the range 5–20 kg/tonne, and in many cases the amount is more than 10 kg/tonne.

The following are three practical examples, illustrating the invention:

EXAMPLE 1

| Ingredients of powder | |
|---|---|
| Chlortetracycline (15% Feed grade) | 2.67 kg |
| Sodium carboxymethylcellulose (high viscosity grade) (Blanose 7HF, Aqualon, France) | 0.50 kg |
| Lactose | 0.81 kg |
| Potassium Sorbate | 0.02 kg |

All ingredients are thoroughly blended dry in a planetary mixer for 12 minutes, and the product transferred into polythene-lined sachets and heat-sealed. The product is used by adding sufficient water to a mixing vessel (eg. planetary mixer bowl) so that the suspending agent forms a 2.5% w/v solution. (For example, 1 kg of product is blended with 5 liters of water.) The suspension is formed by mixing vigorously for 10 minutes.

Once the product is suspended and the gel is sufficiently hydrated it is ready to coat the feed pellets. The pellets are weighed into a suitable mixer (eg ribbon blender) and the required amount of gel added to give the medication level required (eg for 400 mg/kg, add 20 liters/tonne). The mixture is blended for 5 minutes and dispensed into paper sacks.

In a test, the resultant coated feed, when analysed for chlortetracycline content, gave a mean value of 412.6 mg/kg, with a coefficient of variation over 10 assays of 4.6%. The amount of contamination of the mixer as a percentage of the total chlortetracycline added was 0.023%.

EXAMPLE 2

| Ingredients of powder | |
|---|---|
| Sulphadiazine | 0.25 kg |
| Trimethoprim | 0.05 kg |
| Sodium carboxymethylcellulose (high viscosity grade) (Walocel CRT 30000 PA, A. Branwell, England) | 0.50 kg |
| Lactose | 1.20 kg |

The product is prepared by-dry blending as in Example 1. The suspension is formed by mixing 2 kg of product with 20 liters of water as above. To obtain 300 mg/kg of combined actives in the feed, 20 liters of gel is added per tonne of feed, and blended for 5 minutes.

The coated pellets produced by these methods are found to have even distribution of medicament and good durability upon handling. The mixing vessel becomes coated with gel only to a minimal extent.

EXAMPLE 3

| Ingredients of gel | |
|---|---|
| Potassium penicillin V | 0.14 kg |
| Colloidal anhydrous silica (Aerosil 200, Degussa Ltd) | 0.20 kg |
| Dewaxed Sunflower seed oil | 3.66 kg |

The product is prepared by mixing the silica thoroughly with the oil to form a viscous gel base. Then the penicillin is blended into the mixture by using a high shear blender over 20 minutes. The product is packed into polypropylene pails and allowed to reach maximum viscosity. After 24 hours standing the viscosity is 18000 cP (Brookfield RV, spindle 6, 25 rpm, 20 ° C.).

In a full scale test mix approximately 1.5 kg of product was added to 450 kg of feed pellets in a paddle mixer and mixed for 1 minute.

The result of the mean assay of ten subsamples of the coated feed was 106.2 mg/kg (106.20% of nominal) with a coefficient of variation of 6.8%.

The amount of contamination of the mixer was quantified as 0.007% of the total drug added.

I claim:

1. A method of accurately and homogeneously incorporating an added ingredient with a particulate animal foodstuff material the method comprising the steps of:

placing a quantity of said particulate animal foodstuff material in a mixer;

adding to said mixer a gel, the amount of gel added being at a loading of up to 20 kg gel per tonne of foodstuff material, said gel containing a gelling agent, the amount of said gelling agent being up to 10% w/w of the final gel and also containing said added ingredient; and mixing said gel with said particulate animal foodstuff material so that the individual particles of said particulate animal foodstuff material become substantially homogeneously coated with said gel, and the walls of the mixer are left substantially free from added ingredient contamination after mixing.

2. A method according to claim 1, wherein the gelling agent is selected from the group consisting of a modified cellulose polymer, a synthetic polymer, a natural polysaccharide, a clay, a protein, and colloidal silica.

3. A method according to claim 1, wherein said gel is a mixture of a powder comprising said gelling agent and said added ingredient with a solvent or suspension medium.

4. A method according to claim 3, wherein said suspension medium is selected from the group consisting of aqueous and non aqueous media.

5. A method according to claim 1, wherein said added ingredient is a medicament.

6. A method according to claim 5, wherein the medicament is selected from the group consisting of an antimicrobial, an antiprotozoal and an antiparasitic.

7. An animal foodstuff comprising particulate animal foodstuff material and an added ingredient, produced by a method according to claim 1.

8. An animal foodstuff according to claim 7, wherein the form and composition of said foodstuff are suitable for feeding to animals selected from the group consisting of cattle, pigs and fowl.

9. A powder mixture comprising a gelling agent and an ingredient to be added to an animal foodstuff, the powder mixture being suitable for use in a method according to claim 3.

10. A gel manufactured from a powder mixture according to claim 9.

11. A method according to claim 1, wherein said added ingredient is selected from the group consisting of a growth promoter, a vaccine, a mineral, a vitamin, an immunostimulant, or an enzyme, and combination of such ingredients.

12. A method according to claim 1, wherein said animal foodstuff material is in pellet form.

* * * * *